United States Patent
Zurdo Schroeder et al.

(10) Patent No.: US 9,393,218 B2
(45) Date of Patent: Jul. 19, 2016

(54) USE OF FILM-FORMING HAIR CARE POLYMERS FROM THE GROUP OF POLYURETHANES AND PHARMACEUTICAL PREPARATIONS AND PATCHES THAT CONTAIN THESE POLYMERS

(75) Inventors: Ines Zurdo Schroeder, Berlin (DE); Patrick Franke, Berlin (DE); Stefan Bracht, Berlin (DE); Claus-Michael Lehr, Saarbrüken (DE); Ulrich Schäfer, Sulzbach (DE)

(73) Assignee: EPINAMICS GMBH, Berlin (DE)

( * ) Notice: Subject to any disclaimer, the term of this patent is extended or adjusted under 35 U.S.C. 154(b) by 978 days.

(21) Appl. No.: 11/643,948

(22) Filed: Dec. 22, 2006

(65) Prior Publication Data
US 2007/0248658 A1    Oct. 25, 2007

Related U.S. Application Data (60) Provisional application No. 60/764,796, filed on Feb. 3, 2006.

(30) Foreign Application Priority Data

Dec. 23, 2005  (EP) .................................... 05090347
Feb. 3, 2006   (EP) .................................... 06090023

(51) Int. Cl.
*A61K 9/70*    (2006.01)
*A61Q 19/00*   (2006.01)
(Continued)

(52) U.S. Cl.
CPC ............ *A61K 9/7069* (2013.01); *A61K 8/0208* (2013.01); *A61K 8/87* (2013.01); *A61K 9/7015* (2013.01); *A61K 31/00* (2013.01); *A61K 31/215* (2013.01); *A61K 31/34* (2013.01); *A61K 31/35* (2013.01); *A61K 31/38* (2013.01); *A61K 31/40* (2013.01); *A61K 31/415* (2013.01); *A61K 31/44* (2013.01); *A61K 31/445* (2013.01); *A61K 31/495* (2013.01); *A61K 31/517* (2013.01); *A61K 31/52* (2013.01); *A61K 31/522* (2013.01);
(Continued)

(58) Field of Classification Search
None
See application file for complete search history.

(56) References Cited

U.S. PATENT DOCUMENTS

| | | | |
|---|---|---|---|
| 4,997,643 A | 3/1991 | Partain, III et al. | |
| 5,238,933 A * | 8/1993 | Catz et al. | 514/236.2 |

(Continued)

FOREIGN PATENT DOCUMENTS

| | | |
|---|---|---|
| DE | 694 01 230 T2 | 4/1997 |
| EP | 0 619 111 | 10/1994 |

(Continued)

OTHER PUBLICATIONS

International Search Report for International Application No. PCT/EP2006/012635 dated Feb. 22, 2007.

(Continued)

*Primary Examiner* — Trevor Love
(74) *Attorney, Agent, or Firm* — Miller, White, Zelano, Branigan, P.C.

(57) ABSTRACT

The subject of this application is the use of film-forming polyurethanes that are used in hair care agents or mixtures of these polyurethanes with other polymers in pharmaceutical preparations for dermal or transdermal administration of active ingredients, as well as patches and pharmaceutical preparations that contain these hair care polyurethanes.

38 Claims, 4 Drawing Sheets

(51) Int. Cl.
*A61K 8/87* (2006.01)
*A61K 8/02* (2006.01)
*A61K 31/00* (2006.01)
*A61K 31/215* (2006.01)
*A61K 31/34* (2006.01)
*A61K 31/35* (2006.01)
*A61K 31/38* (2006.01)
*A61K 31/40* (2006.01)
*A61K 31/415* (2006.01)
*A61K 31/44* (2006.01)
*A61K 31/445* (2006.01)
*A61K 31/495* (2006.01)
*A61K 31/517* (2006.01)
*A61K 31/52* (2006.01)
*A61K 31/522* (2006.01)
*A61K 31/54* (2006.01)
*A61K 31/55* (2006.01)
*A61K 31/70* (2006.01)
*A61K 36/00* (2006.01)
*A61K 36/28* (2006.01)
*A61K 36/82* (2006.01)
*A61K 36/886* (2006.01)
*A61K 38/28* (2006.01)
*A61K 38/29* (2006.01)

(52) U.S. Cl.
CPC .............. *A61K 31/54* (2013.01); *A61K 31/55* (2013.01); *A61K 31/70* (2013.01); *A61K 36/00* (2013.01); *A61K 36/28* (2013.01); *A61K 36/82* (2013.01); *A61K 36/886* (2013.01); *A61K 38/28* (2013.01); *A61K 38/29* (2013.01); *A61Q 19/00* (2013.01)

(56) References Cited

U.S. PATENT DOCUMENTS

| | | | |
|---|---|---|---|
| 5,474,783 A * | 12/1995 | Miranda et al. | 424/448 |
| 5,626,840 A * | 5/1997 | Thomaides et al. | 424/70.11 |
| 6,203,812 B1 | 3/2001 | Ehrhard et al. | |
| 6,210,705 B1 | 4/2001 | Mantelle | |
| 6,348,211 B1 | 2/2002 | Mantelle | |
| 6,365,697 B1 | 4/2002 | Kim | |
| 6,395,289 B1 | 5/2002 | Ehrhard et al. | |
| 6,797,262 B2 * | 9/2004 | O'Halloran et al. | 424/78.03 |
| 6,962,691 B1 * | 11/2005 | Lulla et al. | 424/45 |
| 7,459,171 B2 | 12/2008 | Cevc | |
| 7,591,949 B2 | 9/2009 | Cevc | |

| | | | |
|---|---|---|---|
| 2003/0007944 A1 | 1/2003 | O'Halloran | |
| 2003/0190294 A1 * | 10/2003 | Leblanc et al. | 424/59 |
| 2003/0199644 A1 * | 10/2003 | Kim et al. | 525/453 |
| 2004/0115228 A1 | 6/2004 | Costa et al. | |
| 2005/0063926 A1 | 3/2005 | Bathina et al. | |
| 2006/0210528 A1 | 9/2006 | Askill et al. | |

FOREIGN PATENT DOCUMENTS

| | | |
|---|---|---|
| EP | 1 150 661 | 10/2003 |
| JP | 11-514639 | 12/1999 |
| JP | 2004 524421 | 8/2004 |
| RU | 2233156 | 7/2004 |
| RU | 2260445 | 9/2005 |
| WO | WO 97/01327 A | 1/1997 |
| WO | WO 00/00023 A | 1/2000 |
| WO | WO 03/041686 A2 | 5/2003 |

OTHER PUBLICATIONS

European Search Report for European Application No. EP 05 09 0347.
Abstract of DE 69401230 (T2) published Apr. 24, 1997. (esp@cenet database—Worldwide).
Kligman, A. et al. "Preparation of Isolated Sheets of Human Stratum Corneum" Archives of Dermatology, vol. 88, 70-73 (Dec. 1963).
Russian Examination Report dated Dec. 2, 2010, and English translation thereof, in Russian Patent Application No. 2008 125 099/15, filed Dec. 19, 2006.
Martino, G. et al. "Polyurethane-14 AMP-Acrylates Copolymer: A Hair Fixative Technology with "Memory"" Cosmetics & Toiletries, 118(1):49-56 (Jan. 2003).
Luviset® P.U.R. Technical Information. Date Published: Jul. 2005, pp. 1-16, BASF Aktiengesellschaft, Fine Chemicals Division—Cosmetic Solutions, Limburgerhof, Germany.
Australian Office Action issued in Australian Patent Application No. 2006332066 date May 3, 2012.
Japanese Examination Report dated Jun. 29, 2012 in corresponding Japanese Application No. 2008-546292.
Office Action issued in parallel Canadian Patent Application No. 2, 633,599. Office Action Date: Nov. 7, 2012.
Office Action issued in parallel Japanese Patent Application No. 2008-546292. Japanese Publication No: 2009-520742. Office Action Date: Nov. 27, 2012.
English Abstract of Russian Patent Publication No. 2234920 (C2). Publication Date: Aug. 27, 2004. Russian Application No: 20020100356 200000609. (Thomson Innovation Record Review).
English Abstract of Russian Patent Publication No. 2260445 (C2). Publication Date: Sep. 5, 2005. Russian Application No: 200210165A1A. Publication Date: Jul. 5, 2005. (Thomson Innovation Record Review).

* cited by examiner

USE OF FILM-FORMING HAIR CARE POLYMERS FROM THE GROUP OF POLYURETHANES AND PHARMACEUTICAL PREPARATIONS AND PATCHES THAT CONTAIN THESE POLYMERS

This application claims the benefit of the filing date of U.S. Provisional Application Ser. No. 60/764,796 filed Feb. 3, 2006, which is incorporated herein by reference.

The invention relates to the use of film-forming hair care polymers from the group of polyurethanes and pharmaceutical preparations that contain these hair care polymers for dermal or transdermal administration of active ingredients. The pharmaceutical preparations are applied on the skin in liquid form. By evaporation of the likewise contained solvent, they form there a flexible, cosmetically inconspicuous, readily adhering, non-sticky film, from which a controlled release of active ingredient into the skin or through the skin in the systemic circuit is carried out.

The human skin as a target organ of the pharmaceutical substance administration is currently used in two respects. On the one hand, active ingredients are administered locally for treatment of various dermal diseases such as psoriasis or neurodermatitis. On the other hand, active ingredients can be administered transdermally for treatment of systemic diseases and for hormone substitution.

In the case of local administration, semisolid preparations, such as ointments, creams or gels, are predominant. In most cases, the transdermal administration takes place via transdermal therapeutic systems, such as matrix or reservoir patches. In recent years, semi-solid products (hydroalcoholic gels, such as, for example, Testogel®) have also been used for transdermal administration.

In the gel formulations for transdermal administration that are found on the market, the active ingredients that are to permeate as alcoholic solution are present. They are thickened by means of a polymer (for example polyacrylic acid) and applied once daily on the skin in the form of a hydroalcoholic gel.

Since alcohols evaporate quickly, the active ingredients also have only a short time to get into the epidermis. More than 90% of the active ingredient therefore does not get into the blood, but rather for the most part remains on the surface of the skin. The quick loss of the solvent results in a supersaturation, which frequently results in active ingredients crystallizing out. A penetration is then considerably hampered since the active ingredient can diffuse into the skin only in dissolved form.

Active ingredient residues that are not fixed to the skin involve the danger of a dose loss as well as a contamination of clothing or other people.

In particular in the transdermal administration, very frequently large application surface areas are required to transport the necessary amounts of active ingredient through the skin. This requires high gel volumes of several milliliters per single dose. The patients consider this to be impractical and unpleasant in the handling. Finally, control of the release of active ingredient over an extended period with standard gel preparations is not possible.

In contrast to this, a controlled release of active ingredient in the transdermal therapeutic systems is possible, but generally the number of offered dosages is limited for reasons of marketing logistics. An individual, patient-related dosage is therefore possible only to a limited extent. Also, with respect to the contact surface area of the transdermal therapeutic system on the skin, limits are placed on the dosage range. Patches larger than 20 $cm^2$ are uncomfortable to wear owing to the large area of skin to which they are fixed. Other drawbacks are skin irritations that are caused by the adhesive layer of the patch, as well as cosmetic impairments. In addition, the production of transdermal patches requires expensive devices and procedures.

For many of the above-mentioned drawbacks, solutions were already offered in the past. Thus, in EP1150661 B1, a topical spray that contains a film-forming composition and one or more active ingredients is claimed. This spray contains, i.a., film-forming polymers. Applied on the skin, it produces a flexible, readily adhering, breathing film.

The object of this invention is to provide alternative pharmaceutical preparations that—applied on the skin—form a film that is improved relative to the active ingredient permeation compared to known preparations.

This object was achieved according to the invention by the use of a film-forming polyurethane that is usually used in hair care agents or a mixture of this polyurethane with various other polymers in pharmaceutical preparations for dermal or transdermal administration of active ingredients.

It was found, surprisingly enough, that the polyurethanes used in hair care agents exhibit good properties with respect to flexibility, stability on the skin and breathing activity, similar to preparations with known polymers (such as, for example, Eudragit®) in the case of clearly elevated active ingredient permeation.

To this end, the film-forming polyurethanes are dissolved or suspended together with one or more active ingredients in a suitable solvent and with the addition of some adjuvants, and the thus formed pharmaceutical preparation is applied in liquid form on the skin.

The application of the thus formed pharmaceutical preparation on the nail, for example for treating nail psoriasis or nail mycoses (onychomycosis), is also possible.

After the solvent evaporates on the skin, the pharmaceutical preparation forms a thin, flexible invisible film. From the film that is formed, one or more active ingredients can be directed onto the skin via the polymer reservoir that is produced or can be released through the skin into the systemic circuit. The administration method that is proposed here is distinguished by a simple administration, for example by spraying or brushing the pharmaceutical preparation, a flexible dosage and a controllable release of active ingredient over an extended period. The film that is produced shows good adhesion on the skin with low irritation potential and an inconspicuous appearance. By the fixing of the active ingredient in film on the skin, a loss of active ingredient by contact with clothing or a contamination of other people is avoided. Another advantage of this invention is that unlike in the production of transdermal patches, no expensive devices or procedures are required. The various components are dissolved only in the solvent or suspended and decanted. The application of the solution can be carried out independently of the skin condition. In contrast to the patch, which should be applied to a hairless, smooth location, existing hair or wrinkles do not produce any problems.

During the evaporation of the solvent, no recrystallization of the active ingredients that are used takes place. Rather, a supersaturated solution, which shows a high thermodynamic activity, is produced. As a result, the permeation of the active ingredient in the skin is required on a permanent basis. Also, in dried film, the active ingredient does not crystallize out, but rather is present in dissolved form. This allows diffusion within the film, so that the active ingredient can also diffuse to the interface after the film is dried and can be released to the skin. In the formulations, either an individual active ingredient can be added, or several active ingredients (for example estrogens such as ethinylestradiol in combination with gestagens such as levonorgestrel) can be added, which then are transported together or in parallel through the skin. By the hair care polyurethanes, the recrystallization of the active ingredient is avoided and simultaneously its absorption through the skin is promoted thermodynamically.

Hair care polymers that are suitable for use in pharmaceutical preparations according to the invention belong to the group of polyurethanes. The polyurethanes that are used in hair care products, alone or in combination with other polymers, such as, for example, acrylates, are especially well suited for this application, since the films that are formed have a high flexibility with simultaneously greater strength. Examples of suitable polyurethanes can be found in the following list. In the list, polyurethanes are cited according to their trade names. Within the corresponding parentheses, the designation of the polyurethane and the respective current manufacturer are indicated.

Luviseto P.U.R. (polyurethane-1, BASF),

DynamX® (polyurethane-14 and AMP-acrylate copolymer, National Starch and Chemical), Avalure® UR 405, Avalure® UR 425 (polyurethane-2, Noveon), Avalure® UR 445 (polyurethane-4, Noveon), Avalure® UR 450 (polypropyleneglycol-17/isophorone diisocyanate/dimethylpropionic acid copolymer, Noveon)

Aquamere™ A/H (polyvinylpyrrolidone/polycarbamyl/polyglycol ester)

Aquamere™ C (polyvinylpyrrolidone/dimethylaminoethylmethacrylate/polycarbamyl/polyglycol ester)

Aquamere™ S (polyvinylpyrrolidone/dimethiconylacrylate/polycarbamyl/polyglycol ester)

The use of an optionally neutralized, completely reacted, carboxylated linear polyurethane, comprising the reaction product that consists of (1) one or more 2,2-hydroxymethyl-substituted carboxylic acid(s), produced by the formula I, in which R means hydrogen or $C_1$-$C_{20}$-alkyl, present in an amount by weight that is sufficient to produce 0.35-2.25 milliequivalents of carboxyl functionality per gram of polyurethane,

Formel I

[Formula I]

(2) 10-90% by weight, relative to the weight of polyurethane, of one or more organic compound(s), which in each case do not have more than two active hydrogen atoms, and (3) one or more organic diisocyanate(s), present in an amount that is sufficient to react with the active hydrogen atoms of the 2,2-hydroxymethyl-substituted carboxylic acid and the organic compounds, with the exception of hydrogen, to form the carboxylate of the 2,2-hydroxymethyl-substituted carboxylic acid, is preferred.

The 2,2-hydroxymethyl-substituted carboxylic acids are produced by the formula I Formel I

[Formula I]

in which R means hydrogen or $C_1$-$C_{20}$-alkyl, preferably $C_1$-$C_8$-alkyl. Special examples comprise 2,2-di-(hydroxymethyl)acetic acid, 2,2-di(hydroxymethyl)propionic acid, 2,2-di(hydroxymethyl)butyric acid, 2,2-di(hydroxymethyl)pentanoic acid, etc. The preferred acid is 2,2-di(hydroxymethyl) propionic acid. The 2,2-hydroxymethyl-substituted carboxylic acids are present in an amount that yields 0.35-2.25, preferably 0.5-1.85, milliequivalents of carboxyl functionality per gram of polyurethane, and in general this is about 5-30% by weight of the polyurethane polymer.

The organic compounds, which react with isocyanate and can be used for the production of the polyurethane polymers according to the invention, have no more than two active hydrogen atoms (determined according to the Zerewitinoff method). The active hydrogen atoms are normally bonded to oxygen, nitrogen or sulfur atoms. These compounds have a molecular weight of about 300 to 20,000, preferably about 500 to 8,000. The compounds are preferably linear to avoid gelling during the polymerization, but small amounts of non-linear compounds can be used with the proviso that their use does not lead to any gelling. The organic compounds are present in an amount of 10-90% by weight, preferably in an amount of 15-70% by weight, of the polyurethane.

The preferred organic compounds with two active hydrogen atoms are the linear bifunctional polyethylene and polypropylene glycols, in particular those that are commercially available and are produced by reaction of ethylene oxide (or propylene oxide) with water, ethylene glycol (or propylene glycol) or diethylene glycol (or dipropylene glycol) in the presence of sodium hydroxide as a catalyst. These polyglycols have molecular weights of about 600 to 20,000, preferably about 1,000 to 8,000. Polyglycols with homogeneous molecular weight or a mixture of glycols with different molecular weights can be used. It is also possible to incorporate small amounts of additional alkylene oxides by copolymerization into the polyglycol.

Other suitable organic compounds with two active hydrogen atoms are those that have hydroxyl, carboxyl, amino or mercapto groups. Among them, polyhydroxy compounds, such as polyether diols, polyester diols, polyacetal diols, polyamide diols, polyester polyamide diols, poly(alkylene ether) diols, polythioether diols and polycarbonate diols are preferred. Compounds with two or more different groups within these classes, for example amino alcohols and amino alcohols with two amino groups and one hydroxyl group, can also be used. Bifunctional compounds are preferably used, although small amounts of tri- (and multi-) functional compounds can also be used.

Suitable polyether diols are, for example, the condensation products that consist of ethylene oxide, propylene oxide, butylene oxide or tetrahydrofuran and their co-, graft or block polymerization products, such as mixed ethylene oxide, propylene oxide condensates and the graft polymerization products from the reaction of olefins that are under high pressure with the mentioned alkylene oxide condensates. Suitable polyethers are produced by condensation of the above-mentioned alkylene oxides with multivalent alcohols, such as ethylene glycol, 1,2-propylene glycol and 1,4-butanediol.

Suitable polyester diols, polyester amide diols, and polyamide diols are preferably saturated and are obtained by, for example, reaction of saturated or unsaturated polycarboxylic acids with saturated or unsaturated multivalent alcohols, diamines or polyamines. For the production of these compounds, suitable carboxylic acids comprise, for example, adipic acid, succinic acid, phthalic acid, terephthalic acid, and maleic acid. For the production of polyesters, suitable multivalent alcohols comprise, for example, ethylene glycol, 1,2-propylene glycol, 1,4-butanediol, neopentyl glycol and hexanediol. Amino alcohols, such as ethanolamine, are also suitable. For the production of polyester amides and polyamides, suitable diamines are, for example, ethylenediamine and hexamethylenediamine.

Suitable polyacetals can be produced from, for example, 1,4-butanediol or hexanediol and formaldehyde. Suitable polythio ethers can be produced by, for example, condensation of thiodiglycol alone or combined with other glycols, such as ethylene glycol, 1,2-propenylene glycol, or with other polyhydroxy compounds, as previously disclosed. Polyhydroxy compounds, which already contain urea or urethane groups, and natural, multivalent alcohols, which can be further modified, for example castor oil and carbohydrates, can also be used.

In the production of the polyurethane polymer, it may be desirable to subject the polymer, in addition to the organic compound, with not more than two active hydrogen atoms, which in many cases has a high molecular weight, with use of an organic compound with a lower molecular weight, preferably of less than about 300 and more than 60, to a chain lengthening. Typical chain-lengthening agents comprise saturated or unsaturated glycols, such as ethylene glycol, diethylene glycol, triethylene glycol, etc.; amino alcohols, such as ethanolamine, propanolamine, butanolamine, etc.; mono- and di-alkoxylated aliphatic, cycloaliphatic, aromatic and heterocyclic primary amines, such as N-methyl diethanolamine, N-oleyidiethanolamine, N-cyclohexyldiisopropanolamine, N,N-dihydroxyethyl-p-toluidine, N,N-dihydroxypropylnaphthylamine, etc.; diamines, such as ethylenediamine, piperazine, N,N-bis-gamma-aminopropyl-N-methylamine, etc.; carboxylic acids, including aliphatic, cycloaliphatic, aromatic and heterocyclic dicarboxylic acids, such as oxalic acid, malonic acid, succinic acid, glutaric acid, adipic acid, sebacic acid, terephthalic acid, naphthalene-1,5-dicarboyxlic acid, maleic acid, fumaric acid, diglycolic acid, quinolinic acid, lutidinic acid, etc.; aminocarboxylic acids, such as glycine, alpha- and beta-alanine, 6-aminocaproic acid, 4-aminobutyric acid, p-aminobenzoic acid, and 5-aminonaphthoic acid, etc. The preferred chain-lengthening agents are aliphatic diols.

The organic polyisocyanates or mixtures of polyisocyanates, which can be reacted with the organic compound, are aliphatic or aromatic polyisocyanates or mixtures thereof. The polyisocyanates are preferably diisocyanates, thus a linear polymer is produced, although small amounts of trifunctional isocyanates together with the diisocyanates can be used. The isocyanate is present in an amount that is sufficient to react with the active hydrogen atoms of the 2,2-hydroxymethyl-substituted carboxylic acid and the organic compounds, with the exception of hydrogen, to form the carboxylate of 2,2-hydroxymethyl-substituted carboxylic acid. This amount varies, based on the amount of carboxylic acid and organic compounds.

Examples of diisocyanates comprise, without, however, being limited thereto, methylenedi-p-phenyldiisocyanate, methylene-bis(4-cyclohexyl isocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 4,4'-dibenzyl diisocyanate, 1,3-phenylene diisocyanate, 1,4-phenylene diisocyanate, mixtures of 2,4- and 2,6-toluene diisocyanate, 2,2'-dichloro-4,4'-diphenylmethane diisocyanate, 2,4-dibromo-1,5-naphthalene diisocyanate, butane-1,4-diisocyanate, hexane-1,6-diisocyanate, and cyclohexane-1,4-diisocyanate.

If it is not desired to lengthen the polymer chain, the reaction of the diisocyanate with the organic compound, which contains two active hydrogen atoms, is brought to a halt by adding a monofunctional compound that contains active hydrogen in order to consume any residual isocyanate functionality. Examples of these chain stoppers are well known in this area of expertise; for this system, the preferred chain stopper is ethanol.

The polymerization of urethanes is performed in the reaction medium with or without, typically, catalysts for the urethane reaction that are known in the area of expertise. Suitable catalysts comprise dibutyltin-dilaurate, tin(II) salts of carboxylic acids with 2 to 18 carbon atoms, such as tin(II) laurate, tin(II) stearate, tin(II) acetate, tin(II) butyrate, tin(II) octoate, etc., as well as mixtures thereof. The other suitable catalysts include dibutyltin oxide, dibutyltin sulfide, lead resinate, lead benzoate, lead salicylate, lead-2-ethyl hexoate, lead oleate, iron acetyl acetonate, cobalt benzoate, tetra(2-ethylhexyl)-titanate, tetrabutyl titanate, etc. Many other compounds accelerate the reaction of a hydroxyl group or another group with an isocyanate rather than certain other reactions of the isocyanate group, and any of these compounds can be used. The experts are to select a special catalyst to impart desirable characteristic features to the individual urethane reactions. The existing special compounds are the preferred compounds and are mentioned as explanatory and not limiting. In addition, any suitable tertiary amine, for example triethylenediamine, N-ethylmorpholine, N-methylmorpholine or 4-dimethylamino-ethylpiperazine, can be used either alone or together with the metal catalyst.

As far as the ratio of the co-reactants is concerned, it should be selected such that the molecular ratio of the isocyanate groups to the active hydrogen atoms is as close as possible to 1:1. Certainly, this exact ratio cannot always be achieved in practice; therefore, a ratio of between about 0.7:1 and 1.3:1 and preferably between about 0.9:1 and 1.2:1 should be sought, and any excess diisocyanate can, as previously discussed, be suppressed with the monofunctional compound that contains active hydrogen.

The polymerization is performed according to known polymerization processes for the production of polyurethane that are well known to the experts. By way of example, polymerization processes and reaction conditions are indicated in the examples of DE69401230T2.

The use of the polyurethane-14-AMP-acrylate copolymer (DynamX®) is especially preferred.

The hair care polymers from the group of polyurethanes that are listed above form cosmetically inconspicuous and flexible films on the skin. Cosmetically inconspicuous and flexible films are then always present if the formed film is transparent and is barely or only moderately fixed to the skin. A strong attachment to the skin would result in undesirable wrinkling. The wearing comfort and the cosmetic attractiveness would be reduced. During a wearing time of at least 24 hours, the films show a sufficient adhesion (i.e., no peeling off or detaching) and have so high a flexibility that during this time, no visible cracks form. An extended wearing period of 72-84 hours—this corresponded to a twice-weekly administration—is also conceivable.

The pharmaceutical composition according to the invention in this case combines a simple administration and a flexible dosage. It is quick-drying, non-sticky and readily adhesive. The release of active ingredients can be controlled over an extended period. For hormones, a higher active ingredient permeation through the human epidermis than in the hormone patches that are usual in the market or from ethanolic hormone solutions of the same concentration is reached in this case. There is no contamination of clothing or other people.

For viscosity and cosmetic reasons, the concentration of the film-forming hair care polyurethane in the pharmaceutical preparations must move only within specific limits. An excessive polymer proportion results in a considerable increase in viscosity. An administration, for example by spraying, would thus be hampered. Another result would be the formation of films that are too thick, which in turn would cause a strong fixing to the skin and thus an undesirable wrinkling. The thickness of the polymer films thus formed by application of the pharmaceutical preparation on the skin is above 1 μm and must not exceed 100 μm. Preferred film thicknesses are between 5 μm and 50 μm.

Since the amount of the polyurethane that is contained, however, also has an influence on the active ingredient loading capacity, a concentration range can be set individually for each polyurethane that produces a film that is based on the properties of the polymer and the active ingredient, and said film makes possible an adequate active ingredient permeation over the desired period and at the same time corresponds to the cosmetic requirements (no wrinkling). The polyurethane concentration in the liquid pharmaceutical preparation (without propellants) can in this case take on values of between 0.01 to 40% (w/w), preferably from 5 to 30%.

The polyurethane films, moreover, show only a low occlusivity, i.e., a water vapor permeability of greater than 0.05 $g*cm^{-2}*24\ h^{-1}$ (determination according to Ph. Brit 1993 Appendix XXJ). They are thus also suitable for extended periods of use.

In addition to one or more of the above-mentioned polyurethanes, optionally as a mixture of additional polymers, the pharmaceutical preparation according to the invention also contains at least one suitable solvent as well as at least one active ingredient.

As active ingredients, all pharmaceutically active substances are suitable that can be incorporated into the polyurethane solutions and allow a dermal or transdermal administration in corresponding indications. Also, the administration of active ingredients for therapy of dermal diseases, such as for example, of mycoses, is conceivable by means of the pharmaceutical preparation according to the invention. Thus, skin lesions can be treated specifically, for example by spraying with the polyurethane solution. For the treatment of injured skin, attention must be paid especially to the compatibility of the solvent.

The following list names active ingredients that are suitable for administration with the pharmaceutical preparations according to the invention:

For the transdermal administration, the following are suitable:

Androgens, such as testosterone and its esters (such as, for example, testosterone dipropionate), 7-methyl-11-fluoro-19-nortestosterone or 7-methyl-19-nortestosterone Estrogens, such as ethinyl estradiol, mestranol, quinestranol, estradiol, estrone, estrane, estriol, estetrol and conjugated equine estrogens, Gestagens, such as progesterone, hydroprogesterone caproate, levonorgestrel, norgestimate, norethisterone, drospirenone, dydrogesterone, norelgestromin, levonorgestrel, dienogest, lynestrenol, etonogestrel, medrogestone, nestorone and cyproterone acetate m-Cholinoceptor antagonists, such as scopolamine, trospium chloride, tiotropium and homatropine Prostaglandins, such as dinoprost, misoprostol, sulprostone, and gemeprost;

As well as danazol, finasteride, raloxifene, nicotine, oxytocin, nitroglycerin, fentanyl, naloxone, bupropion, clonidine, propranolol, metoprolol, diltiazem, nicardipine, captopril, isosorbide dinitrate, isosorbide mononitrate, dimethyl isosorbide, talinolol, lidocaine, propipocaine, diazepam, midazolam, methyl phenidate, parathormone, rotigotine, insulin, heparin, oxybutynin, sulfaguanidine and/or zidovudine, including their chiral forms and pharmaceutically acceptable salts.

For the dermal application, the following are suitable:

The oligomers of catechins that are included in the tanning materials, oligomers of gallotannins with flavan derivatives, phenocarboxylic acids, gallic acid and esterified sugars of its derivatives Antiseptic agents, such as chlorhexidine, triclosan and ethacridine Antibiotics, such as fusidic acid, erythromycin, roxithromycin, clarithromycin, spiramycin, minocycline, clindamycin, neomycin B, kanamycin, gentamycin, amikacin, tobramycin, netilmicin metronidazole, nimorazole, tinidazole polymyxin B, colistin, tyrothricin, bacitracin, mupirocin and cephalexin Antifungal agents, such as ketoconazole, itraconazole, amphotericin B, griseofulvin, fluconazole, amorolfine, flucytosine, terbinafine, naftifine, ciclopirox, natamycin, nystatin, undecenoic acid and isoconazole Topical corticosteroids, such as methylprednisolone aceponate, clobetasol propionate, mometasone fuorate, hydrocortisone, betamethasone-17-benzoate, prednicarbate, diflucortolone valerate, triamcinilone acetonide, amcinonide, desoxymethasone, fluocortolone and fluticasone Topical immunomodulators (macrolides), such as tacrolimus and pimecrolimus, but also epothilones The antihistamines azelastine, fexofenadine, levocabastine, loratadine, mizolastine, clemastine, bamipine, cetirizine, dimetidine, ketotifen, and emedastine The immunosuppressive agents cyclosporin, azathioprine and mycophenolate mofetil The anthralins cignolin and dithranol The vitamin D3 analogs calcipotriol and tacalcitol The topical retinoids tretinoin, isotretinoin, acitretin, adapalene and tazarotene The cytostatic agents methotrexate, 5-fluorouracil, 5-hydroxytamoxifen, zinc-pyrithione and fludarabin The UV-protective stilbene derivatives The plant extracts green tea extract, Centella asiatica extract, willow bark extract, birch extract, tea tree oil, olive leaf extract, aloe vera extract, marigold extract, passion blossom extract, witch hazel extract, chamomile extract, bearberry leaf extract and licorice root extract, for example as 18β-glycyrrhetic acid (Zn combination) or mixtures thereof, as well as Urea, lactic acid, fumaric acid ester, azelaic acid, hydroquinone, benzoyl peroxide, benzyl benzoate, ketoprofen, ibuprofen, salicylate, naproxen, diclofenac-Na and salts, ketorolac, indomethacin, piroxicam, nicotinamide, dipropyl phthalate, aminopyrine, flufenamic acid, ketotifen, polidocanol, oligonucleotides, si-RNA and ribozymes, RNA decoy nucleotides, aciclovir, penciclovir, idoxuridine, trifluridine, vidarabine, tromantadine, 5-aminolävulinic acid, lidocaine, procaine and cinchocaine, including their chiral forms and pharmaceutically acceptable salts.

In this case, the active ingredient can be present both in dissolved form and as an emulsion or suspension.

The concentration of the active ingredient in the polymer film that is produced from the pharmaceutical preparation depends on the active ingredient level to be achieved. It is dependent on the skin permeation of the active ingredient and optionally on the presence of permeation enhancers in the formulation. In solutions, the amount of active ingredient to be incorporated is limited by the saturation solubility of the active ingredient in the solution. If the latter is exceeded, the active ingredient is present in partially dissolved and partially suspended form. The amount of the active ingredients contained in the pharmaceutical preparation according to the invention is between 0.01 and 30% (w/w), preferably between 0.01 and 15% (w/w).

The polyurethane films according to the invention are very thin systems with limited loading capacity. Therefore, active ingredients are preferably suitable for administration by this system that either have structurally produced a good skin permeation, can be transported very efficiently through the skin by the polymer system per se or a permeation-promoting addition or are highly potent and therefore must be administered only in small doses. In this connection, hormones, primarily estrogens, gestagens, and androgens, especially ethinyl estradiol and levonorgestrel, are especially suitable.

To avoid long waiting periods when the preparation is dried, which can impair the patient compliance, skin-compatible, slightly volatile solvents are used. These are preferably ethanol, isopropanol, ethyl acetate, volatile silicones, acetone and water. The solvent can be used alone or combined with one another. In the case of aqueous solvent mixtures, the proportion of water is preferably below 50% (w/w) based on the otherwise extended drying period.

One or more softeners optionally can be added to the pharmaceutical preparations. Preferred softeners are triethyl citrate, tributyl citrate, acetyl triethyl citrate, acetyl tributyl citrate, triacetin, dibutyl phthalate, tributyl sebacate, diethyl phthalate, propylene glycol, polyethylene glycol, glycerol or castor oil. In this case, the softener content must be adapted to the polyurethane and its concentration, since in the case of a softener content that is too high, the film is sticky. In the case of a softener content that is too low, however, the adhesiveness and flexibility decrease. The film would then flake off or become cracked after a certain time. The proportion of softeners optionally to be added in the pharmaceutical composition according to the invention is preferably between 0.01 and 20% (w/w). The softeners can be used alone or in combination with one another.

In addition, optionally still other pharmaceutically compatible substances such as moisturizers and emulsifiers can be added to the pharmaceutical compositions according to the invention.

As moisturizers, preferably glycerol, sorbitol, propylene glycol, polyethylene glycol or polyvinyl pyrrolidone as well as combinations thereof are suitable. The proportion of the pharmaceutical preparation thereof is preferably between 0.01 and 10% (w/w).

Emulsifiers that are preferred according to the invention are Na-cetylstearyl sulfate, glycerol fatty acid ester, lecithin, fatty alcohols, cholesterol, sorbitan fatty acid ester, polyoxyethylene(POE)-fatty acid ester, POE-fatty acid glycerides, or POE-fatty alcohol ethers. The latter can be added to the pharmaceutical preparation preferably at a proportion of between 0.01 and 10% (w/w).

A control of the transport of the active ingredient from the polymer system over the skin can be carried out both via the selection of a special permeation-promoter or a combination of various substances and via the amount of the substance or substances to be added.

Preferred permeation enhancers that optionally are to be added are selected from the group of laurocaprams, sulfoxides, terpenes or ethereal oils, oleic acid, oleyl alcohol, lauryl acid, propylene glycol, propylene carbonate, N-methyl-pyrrolidone or isopropyl myristate. In this case, the permeation promoters can be used both individually and in combinations. Especially preferred are oleic acid, the terpene R-(+)-limonene and isopropyl myristate. Quite especially preferred are mono-isopropyl myristate and combinations of oleic acid, R-(+)-limonene or isopropyl myristate with propylene glycol, preferably in a 1:1 ratio.

For example, R-(+)-limonene, oleic acid and isopropyl myristate, primarily in combination with propylene glycol, are especially advantageous for the active ingredient ethinyl estradiol. Their proportion of the pharmaceutical preparation is preferably between 0.01 and 15% (w/w).

In addition to the permeation enhancers, the basic solvents, such as, for example, ethanol, ethyl acetate or isopropanol, can also contribute to promoting permeation. However, the active ingredient permeation that consists of a polymer film that is produced from an ethanolic polymer solution is clearly superior to that from an ethanolic active ingredient solution without a polymer. The presence of the organic solvent alone thus does not cause the increased permeation of the active ingredient through the human epidermis. The polymer plays an important role in this process. This observation is also supported in that different amounts of active ingredient from preparations with different polymers are transported through the human epidermis.

In the case of incorporating large amounts of active ingredients or in the addition of pharmaceutical adjuvants to a large extent, the formulation is to be adapted, for example, by increasing the softener content, since the film properties can change, for example, with respect to the adhesiveness by the added substances.

The pharmaceutical preparations according to the invention can be decanted into commercially available applicators and are applied to the skin with their help. In this connection, rollers, pump spray bottles, sprayers, tubes, brush bottles or pipette bottles are especially suitable. In the case of decanting in one sprayer, there is a need for the additional admixing of a propellant. As a propellant, for example, dimethyl ether or combinations of propane and butane can be used. In this case, the dosage of the active ingredients is carried out by means of devices or processes that are known to one skilled in the art.

For ethinyl estradiol and levonorgestrel, it was possible to show that with the new pharmaceutical preparations both with and without permeation enhancers, more active ingredient can be transported through the human epidermis than from an ethanolic solution of the same concentration. The new polymer systems are superior to simple ethanolic solutions of the same active ingredient concentration with respect to the amount of active ingredient that is permeated within 24 hours.

From the pharmaceutical preparation according to the invention, it was possible with and without the addition of permeation enhancers for significantly more ethinyl estradiol per unit of surface area to be transported through the human epidermis within 24 hours than from a commercially available contraceptive patch (EVRA®; active ingredients: ethinyl estradiol and norelgestromin). With the addition of permeation enhancers, just as much levonorgestrel per unit of surface area is permeated within 24 hours through the human epidermis from the pharmaceutical preparation according to the invention as from a commercially available patch for hormone replacement therapy (Fem7® Combi, Phase II; active ingredients: estradiol and levonorgestrel).

BRIEF DESCRIPTION OF THE DRAWINGS

FIG. 5 illustrates graphically the results of a comparison of levonorgestrel skin permeation using a polymer system and levonorgestrel skin permeation from a commercially available patch (Fem7® Combi, Phase II), as described in Example 7; and FIGS. 6-8 illustrate graphically the ethinyl estradiol-plasma levels results for the test described in Example 8.

EXAMPLE 1

Pharmaceutical Preparation without Permeation Enhancers

To find a pharmaceutical preparation without permeation enhancers that dries on the skin in flexible, cosmetically inconspicuous films, an active ingredient to be administered optionally was dissolved while being heated generally in 96% ethanol. After the active ingredient was dissolved, a polymer was added, and the preparation was stirred on the magnetic stirrer until the polymer was completely dissolved. After a clear solution was obtained, optionally crosslinking agents or softeners were added, and the solution was stirred for another 24 hours. The storage of the polymer solution was carried out in glass vessels that were tightly sealed with a siliconized rubber plug and an aluminum flange cap. Polymers, polymer content, softeners and softener content were varied in these formulation tests.

The thus obtained preparations were rated as described below based on the criteria of viscosity, drying time, stickiness of the outside, cosmetic attractiveness and durability on the skin. To this end, about 50 mg (corresponding to 10 mg/cm$^2$) of the thus obtained preparations were applied on the skin with the help of a metal template.

Five minutes after the preparation was applied on the skin, the drying of the film was examined by putting a glass slide without pressure on the film. The film was regarded as dry if no liquid residues could be detected on the slide after the film was lifted. To ensure good patient compliance, only films that can be considered to be dry after 5 minutes are to be selected.

To examine the stickiness of the outside of the film, a wad of cotton was applied with slight pressure to the dry film. The evaluation was carried out based on the amount of cotton fibers held back by the film.

The cosmetic attractiveness of the film was evaluated visually with the naked eye with respect to the thickness, transparency, and degree of skin attached to the film.

After being in place for 24 hours, the durability of the film on the skin was visually evaluated with a magnifier with a 10× magnification. The fewer cracks and gaps of the film (flaking), the better its quality.

The viscosity of the solutions was evaluated visually in the storage vessel with the purpose of selecting low- to moderately viscous preparations that can be administered by spraying.

A preparation was then regarded as successful if in all of the above-mentioned criteria, the best evaluation (low to medium viscosity, drying after 5 minutes, little or no stickiness of the outside of the film, small thickness, good transparency and only slight attachment to the skin as well as little or no formation of cracks or gaps after 24 hours) was achieved. Any change in the pharmaceutical preparations according to the invention with respect to their contents and their concentration has the result of a change in the film properties, which can lead to a change in the evaluation of the above-mentioned criteria. Within certain limits, these changes are acceptable, so that concentration spans for the individual components can be indicated. Strong deviations, however, result in polymer films on the skin that no longer have the desired properties described and thus are no longer suitable for the planned use.

The table below contains data on the quantity ranges within which the pharmaceutical preparations form a flexible, readily adhering, non-sticky and cosmetically inconspicuous film on the skin.

|  | Quantity range | Example 1 |
| --- | --- | --- |
| DynamX ® | 0.1-40% (w/w) | 10% (w/w) |
| Triethyl Citrate | 0.1-18% (w/w) | 1% (w/w) |
| Water | 0.1-50% (w/w) | 16% (w/w) |
| Ethanol | 32-99.7% (w/w) | 68% (w/w) |
| Active Ingredient | 0.1-30% (w/w) | 5% (w/w) |

A pharmaceutical composition that consists of 10% (w/w) DynamX®, 1% (w/w) triethyl citrate, 16% water, 68% (w/w) ethanol and 5% (w/w) active ingredient forms an especially suitable film.

EXAMPLE 2

Pharmaceutical Preparation with Permeation Enhancers

To increase the transport of the active ingredient through the skin, the permeation-promoting substances can be added to the formulations that are evaluated positively with respect to the above-mentioned criteria.

|  | Quantity Range | A | B | C | D | E | F |
|---|---|---|---|---|---|---|---|
| DynamX ® | 0.1-40% | 10% | 10% | 10% | 10% | 10% | 10% |
| Triethyl Citrate | 0.1-18% | 1% | 1% | 1% | 1% | 1% | 1% |
| Oleic Acid | 0.1-10% | 5% | 2.5% | 1.5% |  |  |  |
| R-(+)-Limonene | 0.1-10% |  |  |  | 5% | 2.5% |  |
| IsopropylMyristate | 0.1-10% |  |  |  |  |  | 5% |
| Propylene Glycol | 0.1-10% |  | 2.5% | 1.5% |  | 2.5% |  |
| Ethanol | 22-99.8% | 62.2% | 62.2% | 62.2% | 62.2% | 62.2% | 62.2% |
| Water | 0.1-50% | 16.8% | 16.8% | 16.8% | 16.8% | 16.8% | 16.8% |
| Active Ingredient | 0.1-30% | 5% | 5% | 5% | 5% | 5% | 5% |

%-Data = means % (w/w)

EXAMPLE 3

Ethinyl Estradiol—Permeation Comparison with Ethanolic Solution

For skin permeation tests, human abdominal skin from plastic surgery operations was used. The skin was freed from the underlying fatty tissue and stored frozen until used. For preparation, round samples from the skin pieces were punched out, and the epidermis was separated by heat separation from the other skin components (Kligman, A. M., Christophers, E., *Preparation of Isolated Sheets of Human Stratum Corneum*. Archives of Dermatology, 1963.88: pp. 702-705). The epidermis was clamped together with a suitable supporting membrane in vertical Franz diffusion cells. As an acceptor medium, more neutral phosphate buffer with 0.5% γ-cyclodextrin was used as a solubilizer. During the entire test, the cells were tempered to 32° C., and the acceptor medium was continuously thoroughly mixed in the cells with a magnetic stirring rod. After the respective formulation was applied on the epidermis (in each case four cells per formulation), a sample was removed at defined times from each cell, and the volume was replaced by fresh acceptor medium. The active ingredient content of the samples was determined without further working-up by HPLC.

Figure 1:
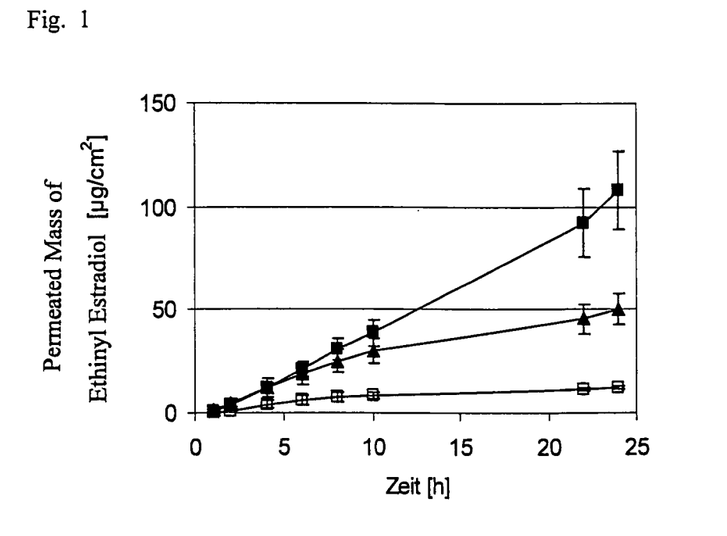
FIG. 1 illustrates graphically the results of the ethinyl estradiol skin permeation tests using a polymer system according to the invention as described in Example 3.

The permeation of ethinyl estradiol was determined from the polymer system according to the invention (DynamX 10% (w/w); ethinyl estradiol content 5% (w/w)) with and without permeation enhancers (oleic acid 2.5% (w/w); propylene glycol 2.5%, (w/w)) by a heat-separated human epidermis and compared to the permeation from an ethanolic solution (5% (w/w) ethinyl estradiol). The results of the permeation tests are shown graphically in FIG. 1/8.

EXAMPLE 4

Ethinyl Estradiol—Permeation Comparison with Patches

Figure 2:
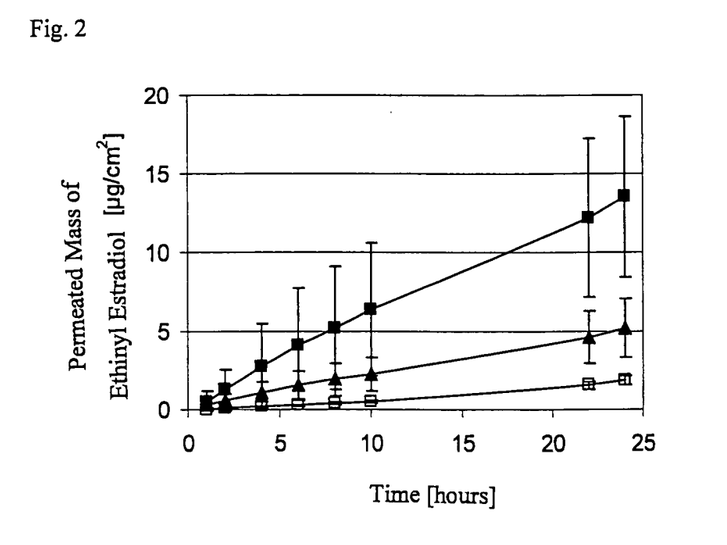
FIG. 2 illustrates graphically the results of the ethinyl estradiol skin permeation tests using a polymer system according to the invention as described in Example 4.

The permeation of ethinyl estradiol from the polymer system according to the invention (DynamX 10% (w/w); ethinyl estradiol content 5% (w/w)) with and without enhancers (oleic acid 2.5% (w/w); propylene glycol 2.5%, (w/w)) was determined by a heat-separated human epidermis and compared to the permeation of ethinyl estradiol from a commercially available contraceptive patch (EVRA®). The results of the permeation tests are shown graphically in FIG. 2/8.

EXAMPLE 5

Ethinyl Estradiol—Permeation Comparison of Different Polymer Solutions

The permeation of ethinyl estradiol from the polymer system according to the invention (DynamX 10% (w/w); ethinyl estradiol content 5% (w/w)) was determined by a heat-separated human epidermis and compared to the permeation of ethinyl estradiol from polymer solutions with other polymers and the same ethinyl estradiol content (5% (w/w)) and with an ethanolic solution (5% (w/w) ethinyl estradiol). The compositions of the tested formulations are cited in the following table:

| Formulation |  | EUD | DYN | KLU | SIL | REF |
|---|---|---|---|---|---|---|
| Polymer |  | Eudragit ® RL PO | DynamX ® | Klucel ® LF | SGM 36 | — |
| Polymer Content | [%] | 20.0 | 10.0 | 5.0 | 10.0 | — |
| Triethyl Citrate | [%] | 6.0 | 1.0 | 1.0 | — | — |
| Ethanol | [%] | 69.0 | 67.2 | 89.0 | 25.0 | 95.0 |
| Water | [%] | — | 16.8 | — | — | — |
| Q7-9180 | [%] | — | — | — | 51.5 | — |
| 193 Fluid | [%] | — | — | — | 8.5 | — |
| Ethinyl Estradiol | [%] | 5.0 | 5.0 | 5.0 | 5.0 | 5.0 |

Figure 3:
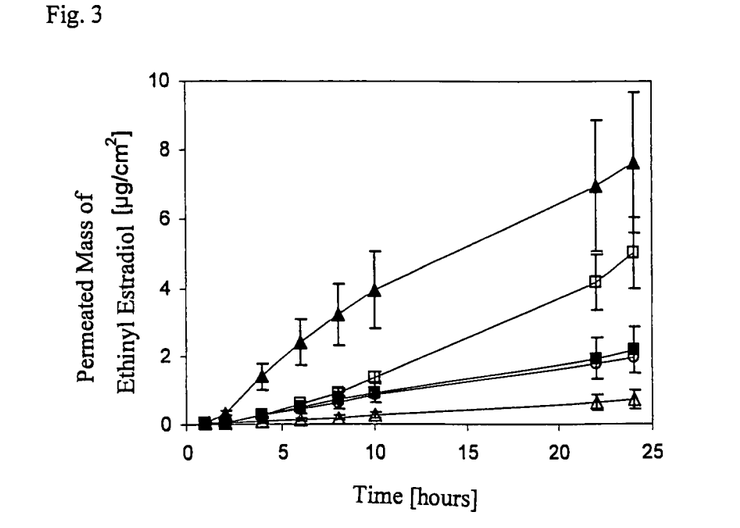
FIG. 3 illustrates graphically the results of the ethinyl estradiol skin permeation tests using a polymer system as described in Example 5.

In this case, Eudragit® RL PO is an ammonium methacrylate copolymer, SGM 36 is a silicone rubber, and Klucel® LF is a hydroxypropyl cellulose. In addition, Q7-9180 means: Dow Corning Q7-9180 Silicone Fluid 0.65 cst (a mixture that consists of hexamethyldisiloxane and octamethyltrisiloxane) and 193 fluid: Dow Corning 193 fluid (PEG-12 dimethicone). The results of the permeation tests are shown graphically in FIG. 3/8.

EXAMPLE 6

Levonorgestrel—Permeation Comparison with Ethanolic Solution

Figure 4:
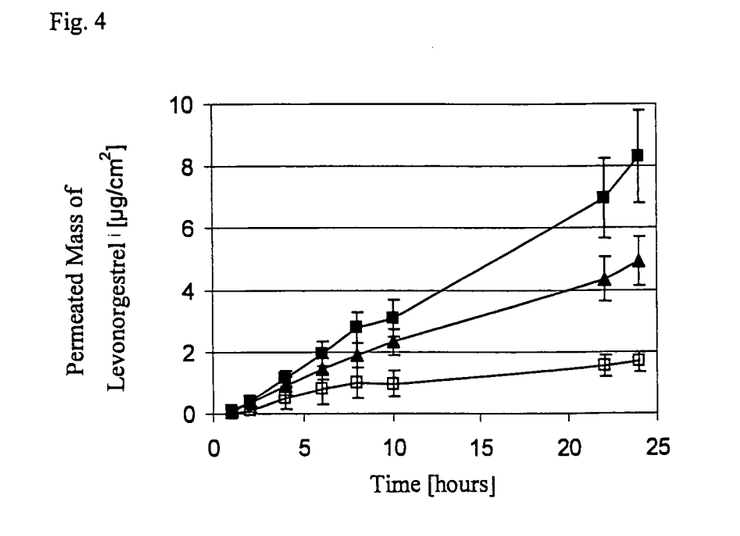
FIG. 4 illustrates graphically the results of a comparison of levonorgestrel skin permeation using a polymer system and levonorgestrel skin permeation from an ethanolic solution, as described in Example 6.

The permeation of levonorgestrel from the polymer system according to the invention (DynamX 10%; levonorgestrel content 0.3% (w/w)) with and without enhancers (oleic acid 2.5%; propylene glycol 2.5%, (w/w)) was determined by a heat-separated human epidermis and compared to the permeation of levonorgestrel from an ethanolic solution (0.3% w/w levonorgestrel). The results of the permeation tests are shown graphically in FIG. 4/8.

EXAMPLE 7

Levonorgestrel—Permeation Comparison with Patches

The permeation of levonorgestrel from the polymer system according to the invention (DynamX 10%; levonorgestrel content 0.3% (w/w)) with enhancer (oleic acid 5.0%; propylene glycol 5.0%, (w/w)) was determined by a heat-separated human epidermis and compared to the permeation of levonorgestrel from a commercially available patch (Fem7® Combi, Phase II). The results of the permeation tests are depicted graphically in FIG. 5/8.

EXAMPLE 8

Determination of the Ethinyl Estradiol Plasma Levels in Pigs After One-time Administration of a Transdermal Patch or a Film-forming Polymer Solution The test was performed with 8 female pigs (German landrace, age 3-4 months) in accordance with the German Animal Protection law and after authorization from the responsible office. The animals were divided into two groups with four animals each. The division was carried out randomly according to weight, so that two groups with similar mean body weight were produced (23.5 kg±0.5 kg). On the day before the experiment, the test area on the back of the animal was shaved without injuring the skin. Before the test medication was administered, the skin was carefully cleaned with alcohol. One EVRA® patch (20 cm$^2$, 0.03 mg of EE/cm$^2$) each was administered to the animals of one group. In the case of the patch detaching during the test (skin contact <90%), the patch was removed and replaced by a new patch on another skin site. 300 µl of the film-forming preparation (composition: 10.0% DynamX®, 1.0% triethyl citrate, 67.2% ethanol, 16.8% water, 5.0% ethinyl estradiol) was administered on 20 cm$^2$ to the animals of the second group. Both preparations were administered in each case once at the beginning of the test. The condition of the medication was observed over the period of the test (7 days) and possible skin reactions were documented. Starting from the time of administration, blood samples were taken after 6 hours, 12 hours, 24 hours, 48 hours, 72 hours, 144 hours and 168 hours, and the plasma per GC-MS on ethinyl estradiol was analyzed.

The ethinyl estradiol-plasma levels can be seen in FIGS. 6/8-8/8. The surface area below the concentration-time curve (AUC$_{0-168\ hours}$) as well as the times of the maximum plasma level (t$_{max}$) are found in the following table.

| Animal No. | t$_{max}$ [hours] | AUC$_{0-168\ hours}$ pg*ml$^{-1}$*h] |
|---|---|---|
| EVRA ® Patch | | |
| 1 | 48 | 146 |
| 2 | 48 | 111 |
| 3 | — | — |
| 4 | 48 | 659 |
| Film-Forming Polymer Solution | | |
| 5 | 72 | 1353 |
| 6 | 24 | 10572 |
| 7 | 6 | 555 |
| 8 | — | 279 |

Both pharmaceutical products showed adequate skin contact over the test period. After administration, the polymer solution formed a clear, bright film on the skin, which after 24 hours began to show cracks. The film could no longer be seen after three to six days. Skin reactions were not observed. Only one animal in the patch group showed a reddening of the skin, which presumably could be attributed, however, to the removal of the patch to be detached. The ethinyl estradiol-plasma levels in both groups showed considerable fluctuations. In the group with the film-forming preparations, moreover, the maximum plasma level was achieved at different times. The calculated surface area under the concentration-time curve was, however, on a higher level in the group with the film-forming preparation than in the patch group. With the aid of the film-forming polymer solution, measurable ethinyl estradiol-plasma levels in vivo could thus be produced in pigs, and said levels had a tendency to be higher than the plasma levels achieved in the patch group.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 05090347.5, filed Dec. 23, 2005 and German application No. 06090023.0 filed Feb. 3, 2006, and U.S. Provisional Application Ser. No. 60/764,796, filed Feb. 3, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A flexible, readily adhesive, non-sticky, cosmetically inconspicuous patch for dermal or transdermal administration of an active ingredient, said patch comprising:
   a transparent, clear film that can be obtained by:
   applying on a patient's skin a pharmaceutical preparation, wherein said pharmaceutical preparation is in the form of a clear, sprayable solution, said pharmaceutical preparation comprising:
   0.1-40% (w/w) of polyurethane-14-AMP-acrylate copolymer;
   0.01-30% (w/w) of one or more active ingredients;
   0.01-20% (w/w) of one or more softeners;
   32-99.7% (w/w) ethanol as solvent;
   up to 50% (w/w) water; and subsequently evaporating said solvent, whereby no recrystallization of the active ingredient occurs and the active ingredient is present in dissolved form in the patch;
wherein said patch has a wearing time of at least 24 hours.

2. A patch according to claim 1, wherein said patch has a water vapor permeability above $0.05 \text{ g*cm}^{-2}\text{*24}^{-1}$.

3. A patch according to claim 1, the amount of polyurethane-14-AMP-acrylate copolymer in said pharmaceutical preparation is 5-30% (w/w).

4. A patch according to claim 1, wherein said pharmaceutical preparation comprises:
optionally 0.01-10% (w/w) of one or more moisturizers,
optionally 0.01-10% (w/w) of one or more emulsifiers, and/or
optionally 0.01-15% (w/w) of one or more permeation enhancers.

5. A patch according to claim 1, wherein said pharmaceutical preparation comprises:
0.01-10% (w/w) of one or more moisturizers,
0.01-10% (w/w) of one or more emulsifiers, and/or
0.01-15% (w/w) of one or more permeation enhancers.

6. A patch according to claim 4, wherein said pharmaceutical preparation is in the form of a solution, emulsion or suspension.

7. A patch according to claim 4, wherein said patch is adapted to provide transdermal administration of said one or more active ingredient.

8. A patch according to claim 7, wherein said one or more active ingredients are selected from:
Testosterone and esters of testosterone, testosterone dipropionate, 7-methyl-11-fluoro-19-nortestosterone, and 7-methyl-19-nortestosterone;
ethinyl estradiol, mestranol, quinestranol, estradiol, estrone, estrane, estriol, estetrol, and conjugated equine estrogens;
progesterone, hydroprogesterone caproate, levonorgestrel, norgestimate, norethisterone, drospirenone, dydrogesterone, norelgestromin, levonorgestrel, dienogest, danazol, lynestrenol, etonogestrel, medrogestone, nestorone, and cyproterone acetate;
finasteride, nicotine, nitroglycerin, fentanyl, clonidine, isosorbide dinitrate, rotigotine, and oxybutynin;
and pharmaceutically acceptable salts thereof.

9. A patch according to claim 8, wherein said one or more active ingredients are selected from: testosterone, testosterone dipropionate, 7-methyl11-fluoro-19-nortestosterone, 7-methyl-19-nortestosterone, and pharmaceutically acceptable salts thereof.

10. A patch according to claim 4, wherein said patch is adapted to provide dermal administration of said one or more active ingredients.

11. A patch according to claim 10, wherein said one or more active ingredients are selected from:
clindamycin, kanamycin, gentamycin, metronidazole, tyrothricin, bacitracin, and mupirocin;
ketoconazole, itraconazole, amphotericin B, griseofulvin, fluconazole, amorolfine, flucytosine, terbinafine, naftifine, ciclopirox, natamycin, nystatin, undecenoic acid, and isoconazole;
methylprednisolone aceponate, clobetasol propionate, mometasone fuorate, hydrocortisone, betamethasone-17-benzoate, prednicarbate, diflucortolone valerate, triamcinilone acetonide, amcinonide, desoxymethasone, fluocortolone, and fluticasone;
tacrolimus and pimecrolimus;
azelastine, fexofenadine, levocabastine, loratadine, mizolastine, clemastine, bamipine, cetirizine, dimetidine, ketotifen, and emedastine;
tretinoin, isotretinoin, acitretin, adapalene, and tazarotene;
diclofenac-Na and salts thereof, aciclovir, penciclovir, idoxuridine, trifluridine, vidarabine, tromantadine, lidocaine, procaine, and cinchocaine;
and pharmaceutically acceptable salts thereof.

12. A patch according to claim 1, wherein said one or more softeners are selected from:
Triethyl citrate,
Tributyl citrate,
Acetyl triethyl citrate,
Acetyl tributyl citrate,
Triacetin,
Dibutyl phthalate,
Dibutyl sebacate,
Diethyl phthalate,
Propylene glycol,
Polyethylene glycol,
Glycerol, and
Castor oil.

13. A patch according to claim 4, wherein said pharmaceutical preparation contains one or more moisturizers selected from: glycerol, sorbitol, propylene glycol, polyethylene glycol, and polyvinyl pyrrolidone.

14. A patch according to claim 4, wherein said pharmaceutical preparation contains one or more emulsifiers selected from: Na-lauryl sulfate, Na-cetyl stearyl sulfate, glycerol fatty acid ester, lecithin, fatty alcohols, cholesterol, sorbitan fatty acid ester, polyoxyethylene fatty acid ester, polyoxyethylene fatty acid glycerides, and polyoxyethylene fatty alcohol ether.

15. A patch according to claim 4, wherein said pharmaceutical preparation contains one or more permeation enhancers selected from: laurocaprams, sulfoxides, terpenes, ethereal oil, oleic acid, oleyl alcohol, lauryl acid, propylene glycol, propylene carbonate, N-methyl-pyrrolidone, and isopropyl myristate.

16. A patch according to claim 4, wherein said pharmaceutical preparation contains one or more permeation enhancers selected from: oleic acid, R-(+)-limonene, isopropyl myristate, mono-isopropyl myristate, a combination of oleic acid with propylene glycol, a combination of R-(+)-limonene with propylene glycol, or a combination of isopropyl myristate with propylene glycol.

17. A patch according to claim 4 wherein said pharmaceutical further contains a propellant.

18. A kit for applying a film-forming pharmaceutical preparation, said kit comprising:
a roller, a pump sprayer, a sprayer, a tube, a brush bottle or a pipette bottle; and
a pharmaceutical preparation in the form of a clear, sprayable solution, said pharmaceutical preparation comprising:
0.1-40% (w/w) of polyurethane-14-AMP-acrylate copolymer;
0.01-30% (w/w) of one or more active ingredients;
a mixture of ethanol and isopropanol;
up to 50% (w/w) water; and
0.01-20% (w/w) of one or more softeners;
wherein said preparation has a wearing time of at least 24 hours.

19. A kit according to claim 18, wherein the amount of said polyurethane-14-AMP-acrylate copolymer is 5-30% by weight of preparation.

20. A patch according to claim 1, wherein said active ingredient is ethinyl estradiol or levonorgestrel.

21. A patch according to claim 1, wherein said pharmaceutical preparation consists essentially of: said polyurethane-14-AMP-acrylate copolymer, said one or more active ingredients, said ethanol as solvent, said one or more softeners, optionally water, optionally one or more moisturizers, optionally one or more emulsifiers, and optionally one or more permeation enhancers.

22. A patch according to claim 1, wherein said pharmaceutical preparation consists of: said polyurethane-14-AMP-acrylate copolymer, said one or more active ingredients, said ethanol as solvent, said one or more softeners, optionally water, optionally one or more moisturizers, optionally one or more emulsifiers, and optionally one or more permeation enhancers.

23. A patch according to claim 1, wherein said pharmaceutical preparation comprises: 0.1-40% (w/w) polyurethane-14-AMP-acrylate copolymer; 0.1-18% (w/w) triethyl citrate; 0.1-50% (w/w) water; said ethanol as solvent, and 0.1-30% (w/w) active ingredient.

24. A patch according to claim 23, wherein said pharmaceutical preparation comprises: 10-40% (w/w) polyurethane-14-AMP-acrylate copolymer; 0.1-18% (w/w) triethyl citrate; 0.1-50% (w/w) water; said ethanol as solvent, and 5-30% (w/w) active ingredient.

25. A patch according to claim 23, wherein said pharmaceutical preparation comprises: 0.1-40% (w/w) polyurethane-14-AMP-acrylate copolymer; 0.1-18% (w/w) triethyl citrate; 0.1-10% (w/w) of permeation enhancers selected from oleic acid, R-(+)-limonene, isopropyl myristate, propylene glycol, and combinations thereof; 0.1-50% (w/w) water; said ethanol as solvent, and 0.1-30% (w/w) active ingredient.

26. A patch according to claim 1, wherein said one or more softeners are selected from triethyl citrate, tributyl citrate, acetyl triethyl citrate, acetyl tributyl citrate, triacetin, dibutyl phthalate, dibutyl sebacate, diethyl phthalate, and castor oil.

27. A patch according to claim 1, wherein said pharmaceutical preparation comprises polyurethane-14-AMP-acrylate copolymer, triethyl citrate, water, said ethanol as solvent, and active ingredient.

28. A patch according to claim 1, wherein said pharmaceutical preparation comprises polyurethane-14-AMP-acrylate copolymer, triethyl citrate, water, said ethanol as solvent, active ingredient, and one or more permeation enhancers.

29. A flexible, readily adhesive, non-sticky, cosmetically inconspicuous patch for dermal or transdermal administration of an active ingredient, said patch comprising:
   a transparent, clear film that can be obtained by applying on a patient's skin a pharmaceutical preparation, wherein said pharmaceutical preparation is in the form of a clear, sprayable solution, said pharmaceutical preparation comprising:
   0.1-40% (w/w) of polyurethane-14-AMP-acrylate copolymer;
   0.01-30% (w/w) of one or more active ingredients;
   0.01-20% (w/w) triethyl citrate as softener;
   a mixture of ethanol and isopropanol;
   up to 50% (w/w) water; and
   subsequently evaporating said solvent, whereby no recrystallization of the active ingredient occurs and the active ingredient is present in dissolved form in the patch;
   wherein said patch has a wearing time of at least 24 hours.

30. A flexible, readily adhesive, non-sticky, cosmetically inconspicuous patch for dermal or transdermal administration of an active ingredient, said patch comprising:
   a transparent, clear film that can be obtained by applying on a patient's skin a pharmaceutical preparation, wherein said pharmaceutical preparation is in the form of a clear, sprayable solution, said pharmaceutical preparation comprising:
   0.1-40% (w/w) of polyurethane-14-AMP-acrylate copolymer;
   0.01-30% (w/w) of one or more active ingredients;
   0.01-20% (w/w) of one or more softeners;
   a mixture of ethanol and isopropanol as solvent;
   up to 50% (w/w) water; and
   subsequently evaporating said solvent, whereby no recrystallization of the active ingredient occurs and the active ingredient is present in dissolved form in the patch;
   wherein said patch has a wearing time of at least 24 hours.

31. A flexible, readily adhesive, non-sticky, cosmetically inconspicuous patch for dermal or transdermal administration of an active ingredient, said patch comprising:
   a transparent, clear film that can be obtained by applying on a patient's skin a pharmaceutical preparation, wherein said pharmaceutical preparation is in the form of a clear, sprayable solution, said pharmaceutical preparation comprising:
   0.1-40% (w/w) of polyurethane-14-AMP-acrylate copolymer;
   0.01-30% (w/w) of one or more active ingredients;
   0.01-18% (w/w) triethyl citrate as softener;
   32-99.7% (w/w) ethanol;
   up to 50% (w/w) water; and
   subsequently evaporating said solvent, whereby no recrystallization of the active ingredient occurs and the active ingredient is present in dissolved form in the patch;
   wherein said patch has a wearing time of at least 24 hours.

32. A flexible, readily adhesive, non-sticky, cosmetically inconspicuous patch for dermal or transdermal administration of an active ingredient, said patch comprising:
   a transparent, clear film that can be obtained by applying on a patient's skin a pharmaceutical preparation, wherein said pharmaceutical preparation is in the form of a clear, sprayable solution, said pharmaceutical preparation comprising:
   0.1-40% (w/w) of polyurethane-14-AMP-acrylate copolymer;
   0.01-30% (w/w) of one or more active ingredients;
   0.01-18% (w/w) triethyl citrate as softener;
   a mixture of ethanol and isopropanol as solvent;
   up to 50% (w/w) water; and
   subsequently evaporating said solvent, whereby no recrystallization of the active ingredient occurs and the active ingredient is present in dissolved form in the patch;
   wherein said patch has a wearing time of at least 24 hours.

33. A patch according to claim 1, wherein said film is dry by 5 minutes after application to said patient's skin.

34. A patch according to claim 29, wherein said film is dry by 5 minutes after application to said patient's skin.

35. A patch according to claim 30, wherein said film is dry by 5 minutes after application to said patient's skin.

36. A patch according to claim 31, wherein said film is dry by 5 minutes after application to said patient's skin.

37. A patch according to claim 32, wherein said film is dry by 5 minutes after application to said patient's skin.

38. A kit for applying a film-forming pharmaceutical preparation, said kit comprising:
   a roller, a pump sprayer, a sprayer, a tube, a brush bottle or a pipette bottle; and a pharmaceutical preparation in the form of a clear, sprayable solution, said pharmaceutical preparation comprising:
0.1-40% (w/w) of polyurethane-14-AMP-acrylate copolymer;
0.1-30% (w/w) of one or more active ingredients;
0.01-20% (w/w) of one or more softeners;
32-99.7% (w/w) ethanol as solvent; and
up to 50% (w/w) water;
wherein said preparation has a wearing time of at least 24 hours.

* * * * *